US00PP25843P3

(12) United States Plant Patent
Schoone

(10) Patent No.: US PP25,843 P3
(45) Date of Patent: Aug. 25, 2015

(54) ***PHALAENOPSIS* ORCHID PLANT NAMED 'GOLD CITY'**

(50) Latin Name: *Phalaenopsis hybrida*
Varietal Denomination: Gold City

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 158 days.

(21) Appl. No.: 13/986,295

(22) Filed: Apr. 19, 2013

(65) Prior Publication Data

US 2013/0291252 P1 Oct. 31, 2013

Related U.S. Application Data

(60) Provisional application No. 61/638,432, filed on Apr. 25, 2012.

(30) Foreign Application Priority Data

Apr. 26, 2012 (NL) ..... PBR OPS915

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Susan McCormick Ewoldt
(74) *Attorney, Agent, or Firm* — Foley & Lardner LLP; Sunit Talapatra

(57) ABSTRACT

A new and distinct *Phalaenopsis* plant named 'Gold City' particularly characterized by flowers which are white/green with purple mark in the center; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Gold City'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Gold City'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Gold City' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Gold City' originated from a cross made by the inventor in 1999 in Strengweg, Heemskerk, The Netherlands. The female or seed parent is the *Phalaenopsis* cultivar designated 'Tzeng-Wen Sentra', unpatented. The male or pollen parent is the *Phalaenopsis* cultivar designated 'Cygnus', unpatented. The new *Phalaenopsis* 'Gold City' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Gold City', which in combination distinguish this *Phalaenopsis* as a new and distinct cultivar:

1. flowers which are green/white with purple mark in the center;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Gold City', the female parent 'Tzeng-Wen Sentra' has red/purple colored flowers and the male parent 'Cygnus' has white colored flowers, whereas the flowers of 'Gold City' are white/green with a purple mark in the center.

Presently, the commercial cultivars to which 'Gold City' can be meaningfully compared are 'Everly Bear' (U.S. Plant patent application Ser. No. 13/986,292) and 'Moondance' (U.S. Plant patent application Ser. No. 13/986,291). The shape of the petals and sepals and the amount of purple marks of the three plants differ. The petals and sepals of 'Gold City' are more ovate/rounder than the petals and sepals of 'Everly Bear' and 'Moondance'. 'Gold City' has the least purple marks. Mainly around the center. 'Everly Bear' has beyond that also a striking large mark on its dorsal sepal. 'Moondance' has even more marks on the petals and sepals than 'Everly Bear'.

BRIEF DESCRIPTION OF THE PHOTOGRAPHS

The accompanying photographs illustrate the overall appearance of the new *Phalaenopsis* 'Gold City' showing the colors as true as is reasonably possible with colored reproductions of this type. Colors in the photographs may differ slightly from the color values cited in the detailed botanical description, which accurately describe the color of 'Gold City'.

DETAILED BOTANICAL DESCRIPTION

Figure 1:
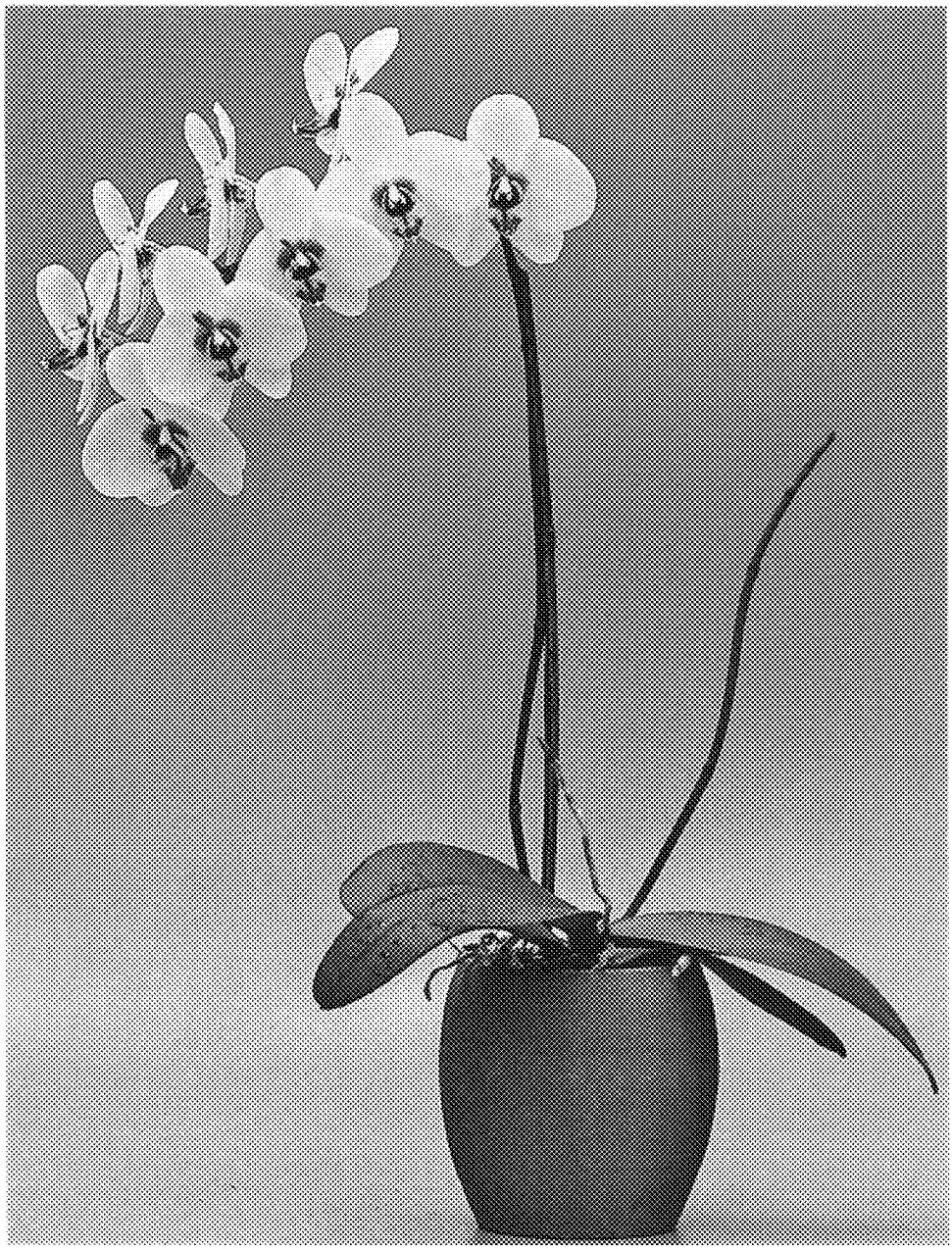
FIG. 1 shows a side view perspective of a typical flowering plant of 'Gold City' in a 12 cm pot, at 16 months of age.

The new *Phalaenopsis* cultivar 'Gold City' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Gold City' as grown in a greenhouse in Strengweg, Heemskerk, The Netherlands, under conditions which closely approximate those generally used in commercial practice. Initially, the ideal temperature to grow plants of 'Gold City' is 27° C. during the day and at night. Then, during the flowering phase of 'Gold City', the ideal growing temperature is 20-22° C. during the day and 18° C. at night. Light levels for growing 'Gold City' are a minimum of 5,000 lux and a maximum of 10,000 lux. A balanced fertilizer with level of 200 ppm N, 87 ppm P, 168 ppm K is applied. Duration of growth of 'Gold City' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Gold City' plants described is 12 months after potting.

Classification:

*Botanical.*—*Phalaenopsis hybrida.*

Parentage:

*Female or seed parent.*—*Phalaenopsis* cultivar designated 'Tzeng-Wen Sentra', unpatented.

*Male or pollen parent.*—*Phalaenopsis* cultivar designated 'Cygnus', unpatented.

Propagation:

*Type.*—Tissue culture.

*Rooting habit and description.*—Fleshy; approximately 3 mm-8 mm wide and green in color (RHS 194C); freely branching. It takes 12 weeks for plants growing in tissue culture to initiate roots.

Plant:

*Size at maturity.*—Height: about 65 cm. Spread: about 55 cm.

*Growth habit.*—Normal; dark-green leaves (RHS 137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-3 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is blunt and asymmetric.

*Texture* (*upper & underside*).—Smooth and leathery.

*Pubescence.*—None.

*Mature leaf length.*—About 15 to 26 cm.

*Mature leaf width.*—About 6 to 10 cm.

*Mature leaf thickness.*—About 2 mm.

*Mature leaf color.*—Upper side: green (RHS 137A). Under side: green (RHS 137C).

*Leaf base.*—Acute.

*Margin.*—Entire.

*Venation.*—Pattern: parallel. Color of midvein: Upper side: green (RHS 137A). Under side: green (RHS 137C).

Inflorescence description:

*Appearance.*—Upright to slightly pendant, racemose inflorescence with bilaterally symmetrical flowers that open in succession beginning with the lowermost flower.

*Raceme.*—Quantity per plant: about 1 to 3. Number of flowers per raceme: about 4 to 10. Length: about 35 cm to 65 cm.

*Peduncle.*—Diameter: about 3 mm to 5 mm. Strength: strong. Aspect: upright. Texture: glabrous and smooth. Color: green (RHS N137B).

*Buds.*—Height (from base to tip): about 22 mm. Diameter (at midpoint): about 18 mm. Shape: egg-shaped. Color: yellow/green (RHS 145C).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 1-3 racemes appear with flower buds and flowers. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
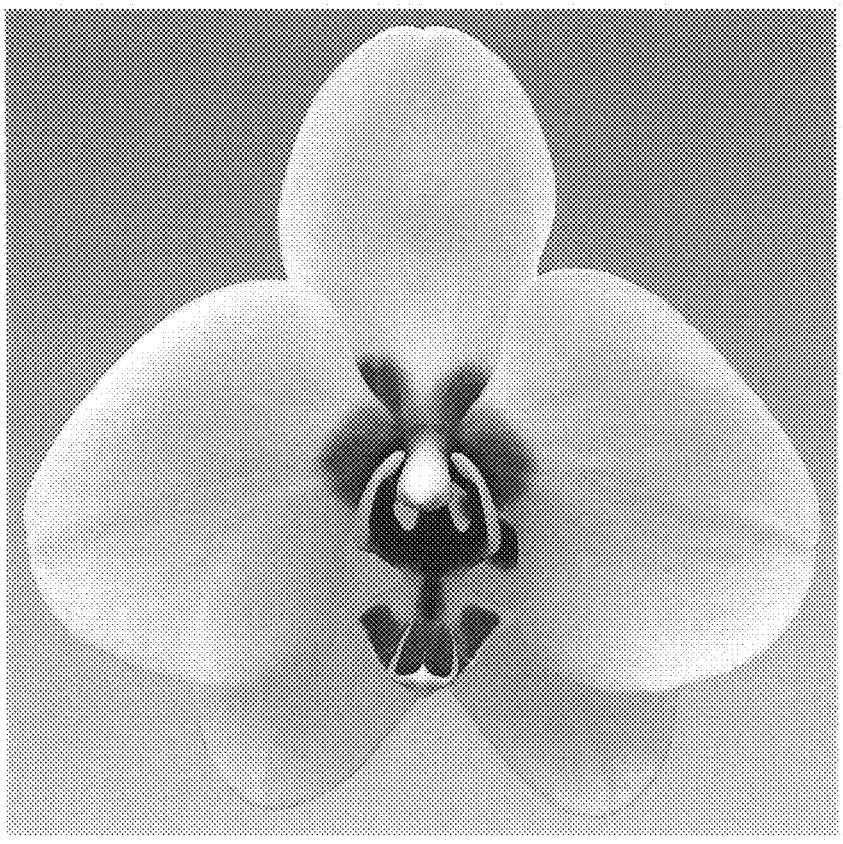
FIG. 2 shows a close-up view of a typical flower of 'Gold City'.
Figure 3:
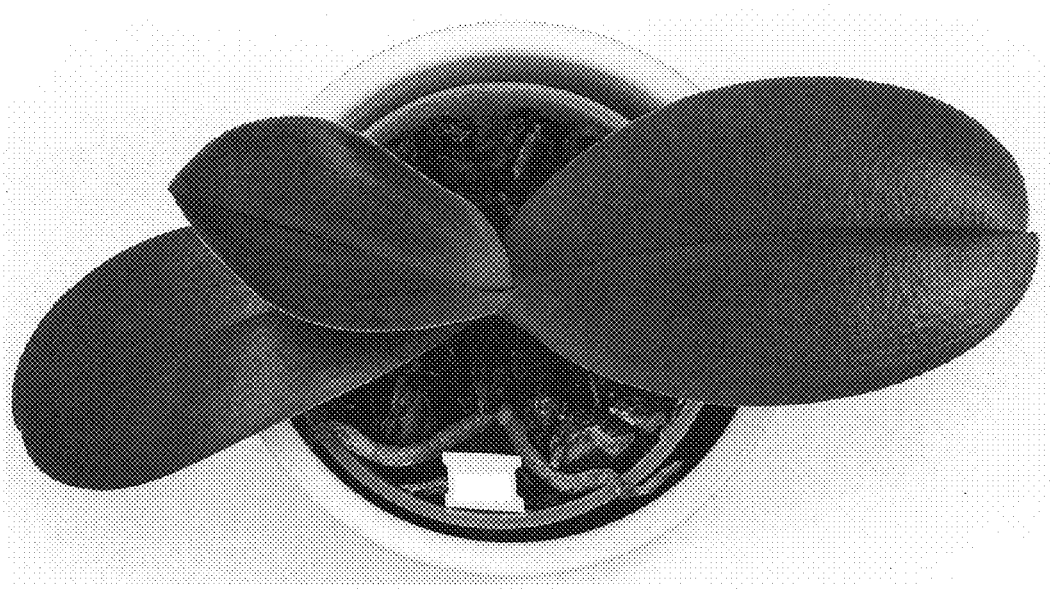
FIG. 3 shows a close-up view of the typical leaves of 'Gold City'.

*Flower.*—Rate of opening: Flowers fully opened about 2 to 3 days after petal and sepal separation. Orientation at opening: slanted upward and outward. Shape: Typical shape of *Phalaenopsis* orchid; see FIG. 2. Size (of single bloom): Height: about 9 cm. Diameter: about 8 and 10 cm. Quantity and arrangement: three petals and three sepals that are trimerous, overlapping and arranged in 2 whorls. Petals are more pronounced than sepals.

*Petals.*—Arrangement: Inner whorl comprises 3 petals: 2 lateral petals and labellum. 2 lateral petals: Overall shape: broadly ovate, little triangular and weakly cupped. Apex: oval. Margin: entire and weakly undulate. Base: broadly ovate. Length: about 5 cm. Width: about 4 cm. Texture: Upper surface: smooth and satiny. Under surface: smooth and satiny. Color (when fully opened): upper side: main color is green/white (combination of RHS 157D and RHS 157B). At the base a red/purple mark (RHS 72A). Under side: main color is green/white (combination of RHS 157D and RHS 157B). At the base a red/purple mark (RHS N79C). Labellum: Overall Representation: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: Lateral lobes: oval. Midlobe: round corners. Length: about 21 mm. Width (not flattened): about 22 mm. Depth of tube created by lateral lobes of labellum: about 12 mm. Texture: Upper and under surface: smooth and satiny. Color (when fully opened): Midlobe: upper surface: At the base grey/purple stripe in the center (RHS 187A), on the edges and in the corners yellow (RHS 14B), with at the very edge orange (RHS 167B). To the center purple (RHS 183C) which runs into red/purple (RHS 72A). On the edges and close to the cirrhi some white (RHS NN155D). Under surface: In the center white (RHS NN155D), on both edges red/purple (RHS 72A) and in the corners close to the base some yellow/orange (RHS 14B). Lateral lobes: upper surface: At the base purple (RHS N79A) which runs into red/purple (RHS 72A) and after that white (RHS NN155D). At the lower edges some yellow (RHS 17B). Under surface: At the base purple (RHS N79A) which runs into red/purple (RHS 72A) and after that white (RHS NN155D). The lower edges are yellow (RHS 17B). Cirrhi: normal (about 6 mm); color: starts white (RHS NN155D) and runs into yellow (RHS 17C). Pestle (Callosities): Length: about 4 mm. Width (not flattened): about 5 mm. Color: grey/purple (RHS 187A), sides brown (RHS 177D), tips on top are yellow (RHS 21C).

*Sepals.*—Arrangement: Outer whorl comprises 3 sepals, one dorsal and two lateral sepals. Overall shape: elliptical and weakly cupped. Margin: entire and weakly undulate. Length: about 45 mm. Width: about 33 mm. Apex: dorsal: oval with a notch; lateral: oval. Texture: Upper and under surface: smooth and satiny. Color (when fully opened): upper surface: green/white (combination of RHS 157B and RHS 157A). At the base some purple marks (RHS 72A). Under surface: yellow/green (some flowers RHS 149D and some flowers RHS 144D with a RHS 157A edge), with purple marks (RHS 77A).

*Pedicel.*—Length: about 35 mm to 50 mm. Diameter: about 3 mm. Texture: glabrous and smooth. Color: Close to the flower yellow/green (RHS 150D) which runs into grey/purple (RHS 187A).

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Length: about 10 mm. Diameter: about 6 mm. Color: white (RHS NN155D) at the base some purple (RHS 72A).

*Pollinia.*—Quantity: two. Diameter: about 1 mm. Color: yellow (RHS 23A).

*Ovary.*—Length: about 3 mm. Diameter: about 1.5 mm. Color: white (RHS NN155D) and purple (RHS 71D).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Gold City', as illustrated and described herein.

* * * * *